(12) United States Patent
Hall et al.

(10) Patent No.: US 7,389,141 B2
(45) Date of Patent: Jun. 17, 2008

(54) BIATRIAL PACING OPTIMIZATION FOR BIVENTRICULAR PACING

(75) Inventors: Jeffrey A. Hall, Birmingham, AL (US); Jiang Ding, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 264 days.

(21) Appl. No.: 10/920,698

(22) Filed: Aug. 18, 2004

(65) Prior Publication Data

US 2005/0137634 A1 Jun. 23, 2005

Related U.S. Application Data (63) Continuation-in-part of application No. 10/744,237, filed on Dec. 22, 2003, now Pat. No. 7,203,540, which is a continuation-in-part of application No. 10/744,944, filed on Dec. 22, 2003, now Pat. No. 7,123,960.

(51) Int. Cl.
*A61N 1/36* (2006.01)
(52) U.S. Cl. .......................................................... 607/9
(58) Field of Classification Search ................ 607/9
See application file for complete search history.

(56) References Cited

U.S. PATENT DOCUMENTS

| | | | |
|---|---|---|---|
| 4,543,963 A | 10/1985 | Gessman | |
| 5,190,035 A | 3/1993 | Salo et al. | |
| 5,237,992 A | 8/1993 | Poore | |
| 5,527,347 A | 6/1996 | Shelton et al. | |
| 5,700,283 A | 12/1997 | Salo | |
| 5,713,928 A | 2/1998 | Bonnet et al. | |
| 5,836,987 A * | 11/1998 | Baumann et al. | 607/17 |
| 6,058,328 A | 5/2000 | Levine et al. | |
| 6,144,880 A | 11/2000 | Ding et al. | |
| 6,161,042 A | 12/2000 | Hartley et al. | |
| 6,219,579 B1 | 4/2001 | Bakels et al. | |
| 6,351,673 B1 | 2/2002 | Ding et al. | |
| 6,360,127 B1 | 3/2002 | Ding et al. | |
| 6,507,756 B1 * | 1/2003 | Heynen et al. | 607/9 |
| 6,542,775 B2 | 4/2003 | Ding et al. | |
| 6,574,506 B2 * | 6/2003 | Kramer et al. | 607/9 |
| 6,597,951 B2 | 7/2003 | Kramer et al. | |
| 6,606,516 B2 * | 8/2003 | Levine | 607/9 |
| 6,684,103 B2 | 1/2004 | Ding et al. | |
| 6,804,555 B2 | 10/2004 | Warkentin | |
| 6,856,836 B2 | 2/2005 | Ding et al. | |

(Continued)

OTHER PUBLICATIONS

Ding, J., et al., "Method and System for Delivering Cardiac Resynchronization Therapy With Variable Atrioventricular Delay", U.S. Appl. No. 10/744,944, filed Dec. 22, 2003, 26 pgs.

(Continued)

*Primary Examiner*—George Manuet
*Assistant Examiner*—Christopher A. Flory
(74) *Attorney, Agent, or Firm*—Schwegman, Lundberg & Woessner, P.A.

(57) ABSTRACT

A method or system for computing and/or setting optimal cardiac resynchronization pacing parameters is presented. Among the parameters which may be optimized in this manner are an atrio-ventricular delay interval, an inter-atrial interval and a biventricular offset interval.

22 Claims, 2 Drawing Sheets

U.S. PATENT DOCUMENTS

| | | | |
|---|---|---|---|
| 6,859,665 | B2 | 2/2005 | Ding et al. |
| 6,871,088 | B2* | 3/2005 | Chinchoy ............... 600/510 |
| 6,904,320 | B2* | 6/2005 | Park et al. ............... 607/17 |
| 6,937,895 | B1 | 8/2005 | Lu |
| 7,123,960 | B2 | 10/2006 | Ding et al. |
| 2003/0144702 | A1* | 7/2003 | Yu et al. ............... 607/17 |
| 2003/0144703 | A1 | 7/2003 | Yu et al. |
| 2003/0204212 | A1* | 10/2003 | Burnes et al. ............ 607/17 |
| 2004/0215258 | A1 | 10/2004 | Lovett et al. |
| 2005/0027323 | A1* | 2/2005 | Mulligan et al. ........ 607/18 |
| 2005/0131472 | A1 | 6/2005 | Ding et al. |
| 2005/0137630 | A1 | 6/2005 | Ding et al. |
| 2005/0137632 | A1 | 6/2005 | Ding et al. |
| 2005/0137633 | A1* | 6/2005 | Salo et al. ............... 607/9 |
| 2006/0041279 | A1 | 2/2006 | Yu et al. |
| 2006/0047320 | A1 | 3/2006 | Ding et al. |
| 2007/0150013 | A1 | 6/2007 | Ding et al. |

OTHER PUBLICATIONS

Ding, J., et al., "Method and System for Setting Cardiac Resynchronization Therapy Parameters", U.S. Appl. No. 10/744,237, filed Dec. 22, 2003, 27 pgs.

Auricchio, Angelo, "Effect of pacing chamber and atrioventricular delay on acute systolic function of paced patients with congestive heart failure". The Pacing Therapies for Congestive Heart Failure Study Group. The Guidant Congestive Heart Failure Research Group, *Circulation*, 99(23), (Jun. 15, 1999), 2993-3001.

"U.S. Appl. No. 10/744,237 Advisory Action mailed Oct. 18, 2006", 3 pgs.

"U.S. Appl. No. 10/744,237 Final office action mailed Aug. 8, 2006", 7 pgs.

"U.S. Appl. No. 10/744,237 Non Final office action mailed Feb. 23, 2006", 11 pgs.

"U.S. Appl. No. 10/744,237 Notice of allowance mailed Dec. 1, 2006", 4 pgs.

"U.S. Appl. No. 10/744,237 Response filed May 23, 2006 to Non Final office action mailed Feb. 23, 2006", 7 pgs, "U.S. Appl. No. 10/744,237 Response filed Oct. 10, 2006 to Final office action mailed Aug. 8, 2006", 6 pgs.

"U.S. Appl. No. 10/744,944 Non final office action mailed Dec. 19, 2005", 9 pgs.

"U.S. Appl. No. 10/744,944 Notice of allowance mailed Jun. 2, 2006", 8 pgs.

"U.S. Appl. No. 10/744,944 Response filed Mar. 20, 2006 to Non final office action mailed Dec. 19, 2005", 9 pgs.

"U.S. Appl. No. 11/113,809 Non Final Office Action mailed Mar. 16, 2007", 10 pgs.

"U.S. Appl. No. 11/113,809 Response filed Jul. 16, 2007 to Non Final Office Action mailed Mar. 16, 2007", 8 pgs.

"U.S. Appl. No. 11/113,809 Non-Final Office Action mailed Jan. 8, 2008", 10 pgs.

* cited by examiner

BIATRIAL PACING OPTIMIZATION FOR BIVENTRICULAR PACING

RELATED APPLICATIONS

This application is a continuation-in-part of U.S. patent application Ser. No. 10/744,237, entitled "METHOD AND SYSTEM FOR SETTING CARDIAC RESYNCHRONIZATION THERAPY PARAMETERS", filed on Dec. 22, 2003 now U.S. Pat. No. 7,203,540, and Ser. No. 10/744,944, entitled "METHOD AND SYSTEM FOR DELIVERING CARDIAC RESYNCHRONIZATION THERAPY WITH VARIABLE ATRIO-VENTRICULAR DELAY", filed on Dec. 22, 2003 now U.S. Pat. No. 7,123,960, the disclosures of which are hereby incorporated by reference.

FIELD OF THE INVENTION

The present disclosure pertains to methods and apparatus for treating cardiac disease with electrical therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. Heart failure can be due to a variety of etiologies with ischemic heart disease being the most common. It has been shown that some heart failure patients suffer from intraventricular and/or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction and/or an atrial pace. Appropriate specification of these pacing parameters is necessary in order to achieve optimum improvement in cardiac function, and it is this problem and the resynchronization of the atria with the ventricles with which the present disclosure is primarily concerned.

DETAILED DESCRIPTION

Described herein are a method and system for setting the pacing parameters and/or pacing configuration of a cardiac rhythm management device for delivering resynchronization pacing to the left ventricle (LV) and/or the right ventricle (RV) in order to compensate for ventricular conduction delays and improve the coordination of ventricular contractions. As will be explained in more detail below, one aspect of the disclosure involves the computation based upon collected data related to cardiac output of an optimum atrio-ventricular delay (AVD) interval and/or biventricular offset (BVO) for delivering ventricular resynchronization therapy in an atrial tracking and/or atrio-ventricular sequential pacing mode to patients having some degree of an atrial conduction delay.

1. Exemplary Hardware Platform

Figure 1:
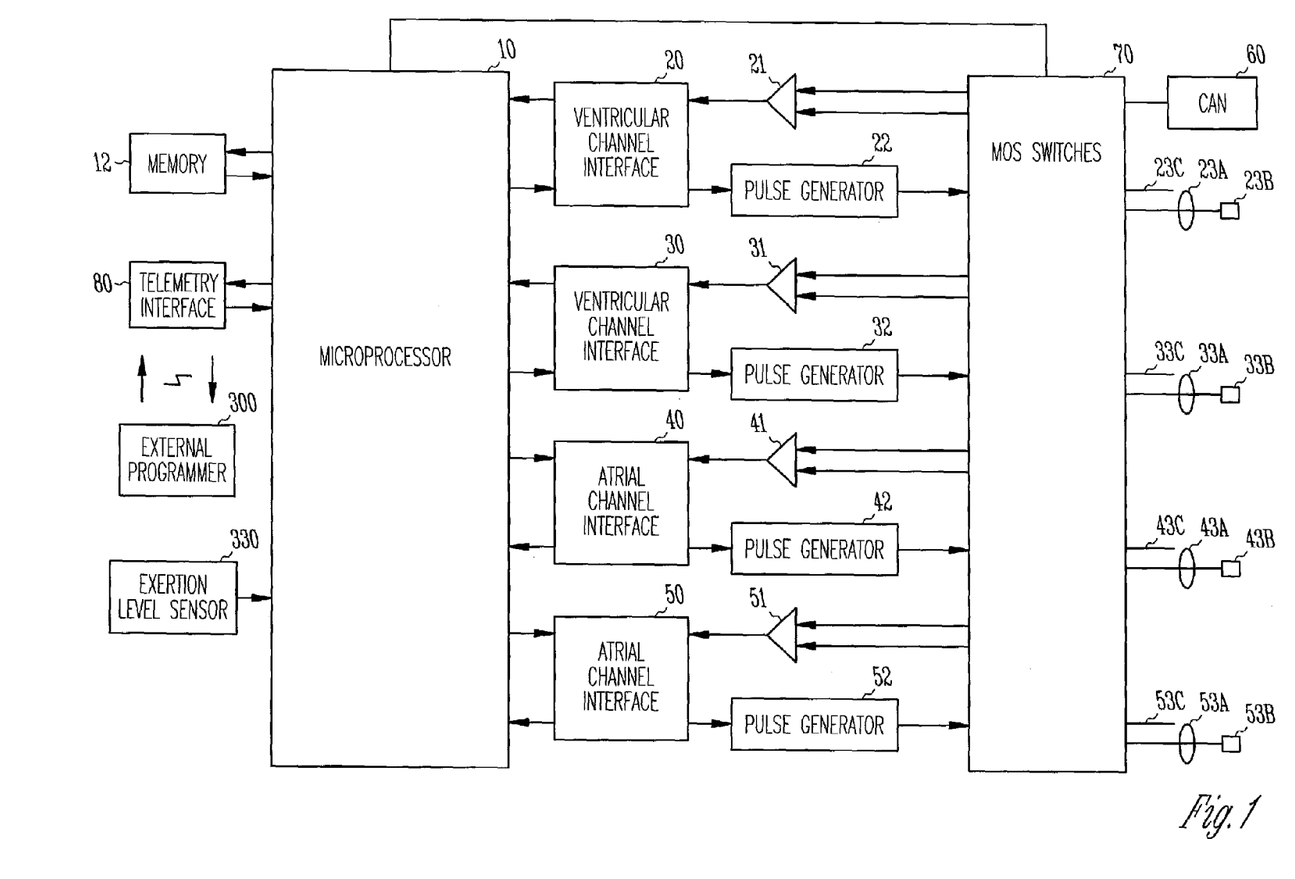
FIG. 1 is a system diagram of exemplary hardware components for delivering cardiac resynchronization therapy.

The following is a description of exemplary hardware components used for practicing the present invention. A block diagram of an implantable cardiac rhythm management device or pulse generator having multiple sensing and pacing channels is shown in FIG. 1. Pacing of the heart with an implanted device involves excitatory electrical stimulation of the heart by the delivery of pacing pulses to an electrode in electrical contact with the myocardium. The device is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

The controller of the device in FIG. 1 is made up of a microprocessor 10 communicating with a memory 12 via a bidirectional data bus, where the memory 12 typically comprises a ROM (read-only memory) and or a RAM (random-access memory). The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry interface 80 is provided for communicating with an external programmer 300. The external programmer is a computerized device with an associated display and input means that can interrogate the pacemaker and receive stored data as well as directly adjust the operating parameters of the pacemaker. As described below, in certain embodiments of a system for setting pacing parameters, the external programmer may be utilized for computing optimal pacing parameters from data received from the implantable device over the telemetry link which can then be set automatically or presented to a clinician in the form of recommendations.

The embodiment shown in FIG. 1 has four sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing with or without atrial tracking, biventricular pacing, or multi-site pacing of a single chamber. In an example configuration, a left atrial sensing/pacing channel includes ring electrode 53a and tip electrode 53b of bipolar lead 53c, sense amplifier 51, pulse generator 52, and a channel interface 50, and a right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing. The switching network 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels and controls the delivery of paces in accordance with a pacing mode. An exertion level sensor 330 (e.g., an accelerometer, a minute ventilation sensor, or other sensor that measures a parameter related to metabolic demand) enables the controller to adapt the atrial and/or ventricular pacing rate in accordance with changes in the patient's physical activity, termed a rate-adaptive pacing mode. The sensing circuitry of the device generates atrial and ventricular electrogram signals from the voltages sensed by the electrodes of a particular channel. An electrogram is analogous to a surface EKG and indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing.

In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax or cardiac anatomy. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output.

2. Cardiac Resynchronization Pacing Therapy

Cardiac resynchronization therapy is most conveniently delivered in conjunction with a bradycardia pacing mode. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. For example, a ventricular escape interval for pacing the ventricles can be defined between ventricular events, referred to as the cardiac cycle (CC) interval with its inverse being the lower rate limit or LRL. The CC interval is restarted with each ventricular sense or pace. In atrial tracking and AV sequential pacing modes, another ventricular escape interval is defined between atrial and ventricular events, referred to as the atrio-ventricular pacing delay interval or AVD, where a ventricular pacing pulse is delivered upon expiration of the atrio-ventricular pacing delay interval if no ventricular sense occurs before. In an atrial tracking mode, the atrio-ventricular pacing delay interval is triggered by an atrial sense and stopped by a ventricular sense or pace. An atrial escape interval can also be defined for pacing the atria either alone or in addition to pacing the ventricles. In an AV sequential pacing mode, the atrio-ventricular delay interval is triggered by an atrial pace and stopped by a ventricular sense or pace. Atrial tracking and AV sequential pacing are commonly combined so that an AVD starts with either an atrial pace or sense. When used in CRT, the AVD may be the same or different in the cases of atrial tracking and AV sequential pacing.

As described above, cardiac resynchronization therapy is pacing stimulation applied to one or more heart chambers in a manner that compensates for conduction delays. Ventricular resynchronization pacing is useful in treating heart failure in patients with interventricular or intraventricular conduction defects because, although not directly inotropic, resynchronization results in a more coordinated contraction of the ventricles with improved pumping efficiency and increased cardiac output. Ventricular resynchronization can be achieved in certain patients by pacing at a single unconventional site, such as the left ventricle instead of the right ventricle in patients with left ventricular conduction defects. Resynchronization pacing may also involve biventricular pacing with the paces to right and left ventricles delivered either simultaneously or sequentially, with the interval between the paces termed the biventricular offset (BVO) interval (also sometimes referred to as the LV offset (LVO) interval or VV delay). The offset interval may be zero in order to pace both ventricles simultaneously, or non-zero in order to pace the left and right ventricles sequentially. As the term is used herein, a negative BVO refers to pacing the left ventricle before the right, while a positive BVO refers to pacing the right ventricle first. In an example biventricular resynchronization pacing mode, right atrial paces and senses trigger an AVD interval which upon expiration results in a pace to one of the ventricles and which is stopped by a right ventricular sense. The contralateral ventricular pace is delivered at the specified BVO interval with respect to expiration of the AVD interval.

Cardiac resynchronization therapy is most commonly applied in the treatment of patients with heart failure due to left ventricular dysfunction which is either caused by or contributed to by left ventricular conduction abnormalities. In such patients, the left ventricle or parts of the left ventricle contract later than normal during systole which thereby impairs pumping efficiency. This can occur during intrinsic beats and during paced beats when only the right ventricle is paced. In order to resynchronize ventricular contractions in such patients, pacing therapy is applied such that the left ventricle or a portion of the left ventricle is pre-excited relative to when it would become depolarized during an intrinsic or right ventricle-only paced beat. Optimal pre-excitation of the left ventricle in a given patient may be obtained with biventricular pacing or with left ventricular-only pacing. Although not as common, some patients have a right ventricular conduction deficit such as right bundle branch block and require pre-excitation of the right ventricle in order achieve synchronization of their ventricular contractions.

3. CRT Pacing Configuration and Mode for Patients with Atrial Conduction Deficit In certain patients, an atrial conduction deficit exists such that left atrio-ventricular synchrony does not occur during intrinsic beats even if the intrinsic atrio-ventricular interval as measured from a right atrial sense to a fight ventricular sense is normal. This is exacerbated by fight atrial pacing and the common location of right atrial appendage pacing. Measurement of the inter atrial conduction times has demonstrated an increase when fight atrial pacing as compared with conduction of an intrinsic atrial event. Additionally there may be an abnormal conduction delay between atria in up to 20% of CRT patients. Another aspect of the present disclosure involves determining if such an atrial conduction deficit exists and adjusting pacing parameters accordingly. It may be implemented in an implantable device for delivering CRT such as illustrated in FIG. 1 which has sensing/pacing channels for both atria and both ventricles. In this embodiment, the implantable device is configured to deliver biventricular pacing in a manner specified by AVD and BVO intervals The device then measures the interval between a right atrial sense or pace and a left atrial sense, referred to as the RA-LA interval. An additional pacing parameter is also provided for pacing the left atrium, if necessary, referred to as the AAL interval which is an escape interval triggered by a right atrial event and results in a left atrial pace upon expiration. If the measured RA-LA interval is above a specified threshold amount, it can be surmised that a conduction deficit exists between the right and left atria. The device can therefore be configured to pace the left atrium at an AAL interval (where a zero AAL interval paces both atria simultaneously) which synchronizes left atrial and left ventricular contractions. In an alternate embodiment, the timing for left atrial pacing may be based upon left ventricular events. This involves pacing the left atrium at a specified offset interval VAL with respect to the time at which a left ventricular pace is delivered A negative VAL interval thus delivers a pace to the left atrium before the left ventricle is paced and may be used in non-atrial triggered and non-AV sequential modes as well atrial triggered and AV sequential pacing modes. In another embodiment, left atrial pacing can based upon both right atrial and left ventricular events so that both AAL and VAL intervals are defined.

4. Optimal Adjustment of Pre-excitation Timing Parameters

Once a particular resynchronization pacing configuration and mode is selected for a patient, pacing parameters affecting the manner and extent to which pre-excitation is applied must be specified. For optimum hemodynamic performance, it is desirable to deliver ventricular pacing, whether for resynchronization pacing or conventional bradycardia pacing, in an atrial tracking and/or AV sequential pacing mode in order to maintain the function of the atria in pre-loading the ventricles (sometimes referred to atrio-ventricular synchrony). Since the objective of CRT is to improve a patient's cardiac pumping function, it is therefore normally delivered in an atrial-tracking and/or AV sequential mode and requires specification of AVD and BVO intervals which, ideally, result in the ventricles being synchronized during systole after being optimally preloaded during atrial systole. That is, both optimal interventricular synchrony and optimal atrio-ventricular synchrony are achieved. As the term is used herein for biventricular pacing, the AVD interval refers to the interval between an atrial event (i.e., a pace or sense in one of the atria, usually the right atrium) and the first ventricular pace which pre-excites one of the ventricles. The AVD interval may be the same or different depending upon whether it is initiated by an atrial sense or pace (i.e., in atrial tracking and AV sequential pacing modes, respectively), The pacing instant for the non-pre-excited ventricle is specified by the BVO interval so that it is paced at an interval AVD+BVO after the atrial event. It should be appreciated that specifying AVD and BVO intervals is the same as specifying a separate AVD interval for each ventricle, designated as AVDR for the right ventricle and AVDL for the left ventricle. In patients with intact and normally functioning AV conduction pathways to the non-pre-excited ventricle, the non-pre-excited ventricle will be paced, if at all, close to the time at which that ventricle is intrinsically activated in order to achieve optimal preloading. In patients with normal AV conduction to the non-pre-excited ventricle, the optimal AVD and BVO intervals are thus related to both the intrinsic atrio-ventricular interval and the amount of pre-excitation needed for one ventricle relative to the other (i.e., the extent of the ventricular conduction deficit).

In order to optimally specify the AVD and BVO parameters for a particular patient, clinical hemodynamic testing may be performed after implantation where the parameters are varied as cardiac function is assessed. For example, a patient may be given resynchronization stimulation while varying pre-excitation timing parameters in order to determine the values of the parameters that result in maximum cardiac performance, as determined by measuring a parameter reflective of cardiac function such as maximum left ventricular pressure change (dP/dt), arterial pulse pressure, or measurements of cardiac output. Determining optimal pacing parameters for an individual patient by clinical hemodynamic testing, however, is difficult and costly. It would be advantageous if such optimal pacing parameters could be determined from data collected by the implantable device. In the approach of the present invention, a variable related to cardiac output, such as transthoracic impedance, is used to compute optimum values of resynchronization pacing parameters. In one embodiment, this allows dynamic changes in device behavior to occur in response to the patient's condition through cardiac remodeling, medication changes and physiologic changes.

In an example embodiment, an implantable cardiac resynchronization device is configured to deliver biventricular pacing in an atrial tracking or AV sequential pacing mode with a specified atrio-ventricular (AVD) interval. The AVD interval (and/or BVO interval) is then varied while measuring a variable related to cardiac output such as transthoracic impedance or intracardiac ultrasound (either external or integral to the device system). The AVD interval can then be set to a value which maximizes the variable related to cardiac output. The AVD interval may be varied, for example, using a binary search algorithm to derive the value of the AVD interval which maximizes the variable related to cardiac output. As described above, an inter-atrial conduction delay which is greater than normal may make it necessary to pace the left atrium in order to achieve optimal synchronization of the left atrium and the left ventricle. The interval from a right atrial sense or pace to a left atrial sense in the patient, designated as the RA-LA interval, is therefore measured, with left atrial pacing initiated if the RA-LA interval exceeds a specified threshold Th1. Additionally following the optimization of the AV delay for maximum cardiac output, the LA-LV timing may be optimized in relationship to maximum cardiac output.

The techniques for setting resynchronization pacing parameters as described herein may be implemented in a number of different ways. In one implementation, a system for setting the pacing parameters includes an external programmer. In an example embodiment, a parameter related to cardiac output is measured by an implantable cardiac resynchronization device equipped with a transthoracic impedance sensor and transmitted to the external programmer via a wireless telemetry link. Either automatically or under the direction of the external programmer, the implantable device then varies the AVD and/or BVO intervals while measuring the variable related to cardiac output and measures the RA-LA interval. In an automated system, the external programmer then automatically programs the implantable device with the computed optimum pacing parameter values, while in a semi-automated system the external programmer presents the computed optimum values to a clinician in the form of a recommendation. An automated system may also be made up of the implantable device alone which collects cardiac output data while varying the AVD and BVO intervals, measures the RA-LA interval and initiates left atrial pacing if necessary, determines the optimum parameter values which maximize cardiac output, and then sets the parameters accordingly. In another embodiment, which may be referred to as a manual system, the external programmer presents the collected cardiac output data and corresponding AVD and BVO intervals, as well as the RA-LA interval to a clinician for evaluation. Unless otherwise specified, references to a system for computing or setting pacing parameters throughout this document should be taken to include any of the automated, semi-automated, or manual systems just described. Another manual system could incorporate manual measurement of CO with external cardiac ultrasound while the device or external programmer optimizes the pacing parameters in a step like fashion.

Figure 2:
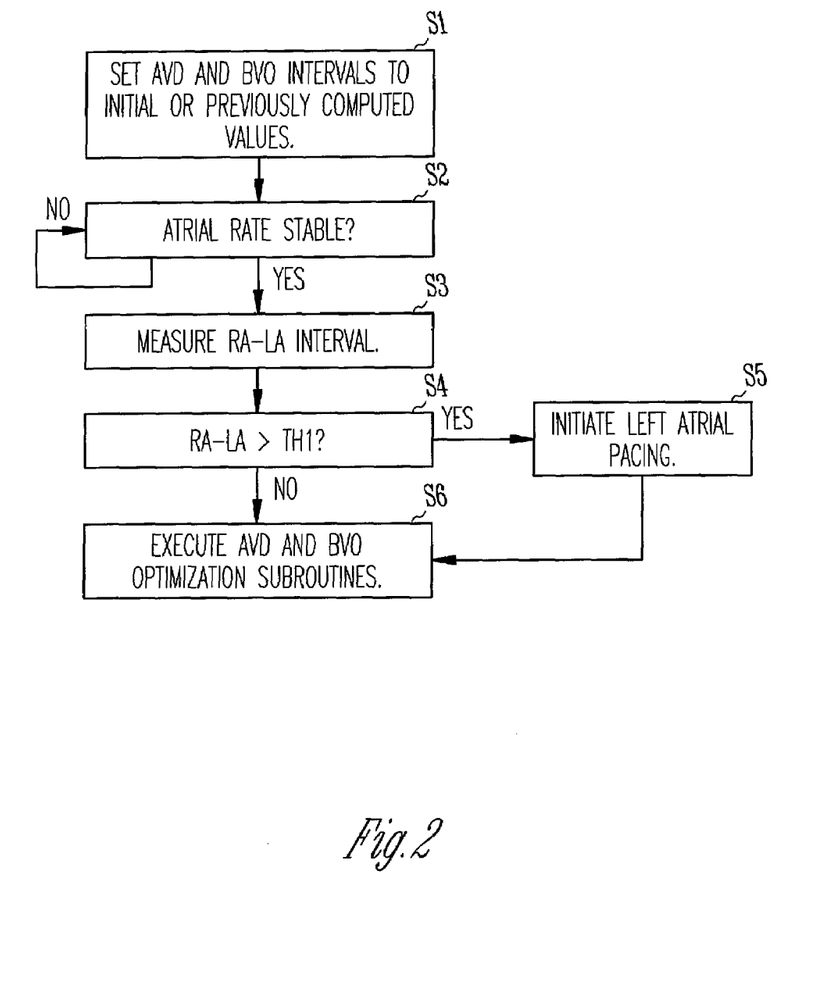
FIG. 2 illustrates an exemplary algorithm for setting pacing parameters.

5. Exemplary Algorithm for Computing Pacing Parameters and Setting Pacing Configuration FIG. 2 illustrates an exemplary algorithm for computing the optimal pacing parameters of an implantable cardiac rhythm management device for delivering biventricular pacing. The algorithm may be partially or wholly implemented as code executed by the device controller or by an external programmer. The implantable device may be equipped with sensing and pacing channels for both ventricles and both atria as shown in FIG. 1. The device is programmed to deliver right and left ventricular paces separated by specified biventricular offset interval BVO and in an atrial tracking or AV sequential mode so that the ventricular paces are delivered at an atrio-ventricular delay interval AVD following an atrial event. At step S1, the AVD and BVO intervals are either set to nominal initial values or are as set by a previous execution of the algorithm. At step S2, the atrial rate (either paced or intrinsic) is measured and tested for stability. If the atrial rate is stable, the RA-LA interval is measured at step S3. The measured RA-LA interval may be either a single measurement or an average of RA-LA interval measurements taken over a number of beats. At step S4, RA-LA interval is compared with a specified threshold value Th1. If the RA-LA interval exceeds Th1, left atrial pacing is initiated at step S5. This will initiate left atrial contraction preceding the left ventricular event mimicking the normal physiologic events. Since this is not a 'normal' heart, minor timing variations may improve cardiac efficiency. For example in the enlarged heart and pathologically damaged left side, left atrial contraction may need to precede the left ventricular event by a greater amount than in the 'normal' healthy heart to allow full LA contraction and atrial augmentation of left ventricular filling. The algorithm then proceeds to step S6 where optimization subroutines are performed for the AVD and BVO intervals. During an optimization subroutine, the interval (either the AVD or BVO) is varied while a variable related to cardiac output is measured, with the optimum value of the interval selected as the interval value which results in maximum cardiac output.

It may be desirable in certain embodiments to make the threshold value Th1 for deciding whether to initiate left atrial pacing depend upon the extent of any AV block which the patient may have. For example, if the patient has normal AV conduction to the right ventricle, the optimum AVD value will normally be very close to the intrinsic atrio-ventricular interval and cannot be lengthened beyond it in order to compensate for an inter-atrial conduction delay. The value of Th1 would then be set to an RA-LA interval value which produces the most left atrio-ventricular dyssynchrony which the algorithm will tolerate without pacing the left atrium. This value of Th1 will be influenced by its relationship to the left ventricular event as well as the right atrial event. If it is desirable to reduce the AV delay to improve cardiac efficiency it may also be beneficial to decrease the inter atrial conduction time below normal physiologic values to optimize left ventricular filling. If the patient has some degree AV block to the right ventricle, on the other hand, the value of Th1 can be set to a larger value before left atrial pacing is initiated. The AVD optimization subroutine, by finding the AVD value which produces maximum cardiac output, will give an AVD interval which is longer than the optimum AVD interval it would find if there were no inter-atrial delay. The optimization subroutine effectively adds the RA-LA interval to the optimum AVD interval which would be found if there were no inter-atrial delay since it is synchrony between the left atria and ventricle that is most responsible for maximizing cardiac output.

In another embodiment, after finding the optimum AVD as measured by cardiac output or other cardiac function, the algorithm may adjust an initial RA to LA timing (perhaps based on averaged measured patient values) through a step up step down algorithm applied to either an AAL or VAL interval used to pace the left atrium, thus optimizing the RA-LA interval and additionally maximizing the cardiac output. The algorithm may also follow optimization of the AVD and RA-LA intervals with re-optimization of the AVD interval to confirm that it was not negatively affected by changing the inter atrial timing.

The algorithm illustrated in FIG. 2 may be performed periodically or upon command from an external programmer. In some situations, it may be desirable for the patient to remain in a steady state during optimization of pacing parameters. Such an optimization procedure may be performed, for example, in a physician's facility or automatically by the implantable device while the patient is sleeping. Optimization of pacing parameters may also be performed during exercise (treadmill testing) since it is expected that these values will change with heart rate. This would allow the computation of dynamic optimum AV delays and inter atrial timing as occurs in the normal physiologic heart. In this manner optimum values for the AVD, BVO, and left atrial pacing intervals may be computed for a plurality of heart rate ranges. For example, the algorithm may first determine which of a plurality of heart rate ranges corresponds to the current measured atrial rate. Optimum AVD, BVO, and left atrial pacing intervals are then computed as described above for that particular heart rate range. The device controller is then programmed to use those optimum AVD, BVO, and/or left atrial pacing interval values which have been computed for the current atrial rate Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for setting optimal pacing parameters for delivering cardiac resynchronization therapy to a patient, comprising:
    delivering biventricular pacing in an atrial tracking or AV sequential pacing mode with a specified atrio-ventricular (AVD) interval;
    measuring the interval from a right atrial sense or pace to a left atrial sense in the patient, designated as the RA-LA interval;
    initiating delivery of left atrial pacing if the RA-LA interval exceeds a specified threshold Th1, wherein the left atrial pacing is delivered at upon expiration of a specified left atrial escape interval triggered by a right atrial event;
    measuring a variable related to cardiac output;
    optimizing the AVD interval in a manner that maximizes cardiac output;
    optimizing the left atrial escape interval in a manner that maximizes cardiac output using the previously optimized AVD interval; and,
    re-optimizing the AVD interval in a manner that maximizes cardiac output using the previously optimized left atrial escape interval.

2. The method of claim 1 wherein the variable related to cardiac output is transthoracic impedance.

3. The method of claim 1 further comprising setting the value of the threshold Th1 in accordance with whether the patient has AV block to the right ventricle.

4. The method of claim 1 wherein the AVD interval is varied using a binary search algorithm to derive the value of the AVD interval which maximizes the variable related to cardiac output.

5. The method of claim 1 further comprising, if no left atrial pacing is being delivered, periodically measuring the RA-LA interval, initiating left atrial pacing if the RA-LA interval exceeds a specified threshold Th1.

6. The method of claim 1 wherein the left atrium is paced at a specified atrial-atrial delay (AAL) interval following a fight atrial sense or pace.

7. The method of claim 1 wherein the left atrium is paced at a specified offset interval preceding a left ventricular event.

8. The method of claim 6 wherein the specified AAL interval varies with heart rate.

9. The method of claim 7 wherein the specified offset interval varies with heart rate.

10. The method of claim 1 wherein the biventricular pacing is delivered with a specified biventricular offset (BVO) interval separating right and left ventricular paces and further comprising:
    varying the BVO interval while measuring a variable related to cardiac output; and,
    computing the optimum BVO interval as the value of the BVO interval which maximizes the variable related to cardiac output.

11. The method of claim 1 further comprising:
    computing optimum AVD and left atrial escape intervals for a plurality of heart rate ranges; and,
    determining which of the plurality of heart rate ranges corresponds to the current measured atrial rate and using the corresponding AVD and left atrial escape interval optimized for that heart rate range.

12. A system for setting optimal pacing parameters for delivering cardiac resynchronization therapy in a biventricular pacing mode to a patient, comprising:
    an implantable cardiac rhythm management device for delivering biventricular pacing, wherein the device is programmed to deliver right and left ventricular paces separated by specified biventricular offset interval BVO and in an atrial tracking or AV sequential mode so that the ventricular paces are delivered at an atrio-ventricular delay interval AVD following an atrial event;
    means for measuring the interval from a right atrial sense or pace to a left atrial sense in the patient, designated as the RA-LA interval;
    means for initiating pacing of the left atrium if the RA-LA interval exceeds a specified threshold Th1, wherein the left atrial pacing is delivered at upon expiration of a specified left atrial escape interval triggered by a right atrial event;
    means for measuring a variable related to cardiac output;
    means for optimizing the AVD interval in a manner that maximizes cardiac output;
    means for optimizing the left atrial escape interval in a manner that maximizes cardiac output using the previously optimized AVD interval; and,
    means for re-optimizing the AVD interval in a manner that maximizes cardiac output using the previously optimized left atrial escape interval.

13. The system of claim 12 wherein the AVD interval setting means is a controller of the implantable device programmed to automatically compute the optimum AVD value and set the AVD parameter to that value.

14. The system of claim 12 further comprising an external programmer for communicating with the implantable device via a wireless telemetry link and wherein the AVD interval setting means is the external programmer which is programmed to automatically compute the optimum AVD value and set the AVD parameter to that value in the implantable device.

15. The system of claim 12 wherein the variable related to cardiac output is transthoracic impedance.

16. The system of claim 12 wherein the value of the threshold Th1 varies in accordance with whether the patient has AV block to the right ventricle.

17. The system of claim 12 wherein the AVD interval is varied using a binary search algorithm to derive the value of the AVD interval which maximizes the variable related to cardiac output.

18. The system of claim 12 wherein the controller is further programmed to deliver left atrial pacing if the RA-LA interval exceeds a specified threshold Th1.

19. The system of claim 12 wherein the implantable device paces the left atrium at a specified offset interval preceding a left ventricular event.

20. The system of claim 12 wherein the implantable device paces the left atrium at a specified atrial-atrial delay (AAL) interval following a right atrial sense or pace.

21. The system of claim 12 further comprising:

means for computing optimum AVD and left atrial escape intervals for a plurality of heart rate ranges; and, means for determining which of the plurality of heart rate ranges corresponds to the current measured atrial rate and using the corresponding AVD and left atrial escape interval optimized for that heart rate range.

22. The system of claim 12 further comprising:

means for varying the BVO interval while measuring a variable related to cardiac output; and, means for setting the BVO interval to a value which maximizes the variable related to cardiac output.

* * * * *

UNITED STATES PATENT AND TRADEMARK OFFICE
CERTIFICATE OF CORRECTION

PATENT NO. : 7,389,141 B2 Page 1 of 1
APPLICATION NO. : 10/920698
DATED : June 17, 2008
INVENTOR(S) : Hall et al.

It is certified that error appears in the above-identified patent and that said Letters Patent is hereby corrected as shown below:

On the title page, in field (63), under "Related U.S. Application Data", in column 1, line 2, delete "which is a" and insert -- and --, therefor.

On the title page, in "Primary Examiner", in column 2, line 1, delete "Manuet" and insert -- Manuel --, therefor.

In column 5, line 44, delete "fight" and insert -- right --, therefor.

In column 5, line 45, delete "fight" and insert -- right --, therefor.

In column 5, line 48, delete "fight" and insert -- right --, therefor.

In column 6, line 7, delete "delivered" and insert -- delivered. --, therefor.

In column 10, line 10, in Claim 6, delete "fight" and insert -- right --, therefor.

Signed and Sealed this

Second Day of September, 2008

JON W. DUDAS
*Director of the United States Patent and Trademark Office*